(12) United States Patent
Ghosh

(10) Patent No.: US 9,750,941 B2
(45) Date of Patent: Sep. 5, 2017

(54) CRITERIA FOR DETERMINATION OF LOCAL TISSUE LATENCY NEAR PACING LEAD ELECTRODES

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/004,487

(22) Filed: Jan. 22, 2016

(65) Prior Publication Data

US 2016/0213928 A1 Jul. 28, 2016

Related U.S. Application Data

(60) Provisional application No. 62/106,940, filed on Jan. 23, 2015.

(51) Int. Cl.
| | |
|---|---|
| *A61N 1/00* | (2006.01) |
| *A61N 1/368* | (2006.01) |
| *A61N 1/365* | (2006.01) |
| *A61B 5/0452* | (2006.01) |

(52) U.S. Cl.
CPC .......... *A61N 1/3684* (2013.01); *A61B 5/0452* (2013.01); *A61N 1/3682* (2013.01); *A61N 1/36514* (2013.01)

(58) Field of Classification Search
CPC .... A61N 1/3627; A61N 1/3684; A61N 1/056; A61N 1/3682; A61N 1/36514; A61N 1/368

See application file for complete search history.

(56) References Cited

U.S. PATENT DOCUMENTS

| | | |
|---|---|---|
| 5,792,212 A | 8/1998 | Weijand |
| 6,418,346 B1 | 7/2002 | Nelson et al. |
| 6,442,433 B1 | 8/2002 | Linberg |
| 6,480,745 B2 | 11/2002 | Nelson et al. |
| 6,599,250 B2 | 7/2003 | Webb et al. |
| 7,778,706 B1 * | 8/2010 | Min ................. A61N 1/36542 607/9 |
| 8,090,443 B2 | 1/2012 | Min et al. |
| 8,738,813 B1 | 5/2014 | Natanzon et al. |
| 9,132,274 B2 | 9/2015 | Ghosh |
| 2008/0086177 A1 | 4/2008 | Min et al. |
| 2011/0144510 A1 * | 6/2011 | Ryu ..................... A61B 5/042 600/509 |
| 2012/0283587 A1 | 11/2012 | Gosh et al. |

* cited by examiner

*Primary Examiner* — Robert N Wieland

(74) *Attorney, Agent, or Firm* — Carol F. Barry

(57) ABSTRACT

A system and method for identifying whether local tissue latency is present. The system and method comprises an implanted lead having a first electrode for cardiac pacing and sensing. A sensing module for sensing heart activity with the first electrode to produce an electrogram (EGM) waveform. A processor is configured to receive the EGM waveform and extract two or more features from the EGM waveform representative of heart activity in response to monoventricular or biventricular pacing stimulus at the electrode and identify local tissue latency at a site of the first electrode based upon at least two of the extracted features indicating local tissue latency.

35 Claims, 5 Drawing Sheets

CRITERIA FOR DETERMINATION OF LOCAL TISSUE LATENCY NEAR PACING LEAD ELECTRODES

CROSS-REFERENCE TO RELATED APPLICATIONS

This application claims the benefit of U.S. Provisional Application No. 62/106,940, filed on Jan. 23, 2015. The disclosure of the above application is incorporated herein by reference in its entirety.

TECHNICAL FIELD

The disclosure relates generally to optimizing control parameters during cardiac pacing therapies; and, more particularly, to optimizing pacing therapy control parameters based on determining the presence of local tissue latency near pacing lead electrodes.

BACKGROUND

Cardiac resynchronization therapy (CRT) is a treatment for heart failure patients. Cardiac resynchronization pacing devices operate by either delivering pacing stimulus to both ventricles or to one ventricle with the desired result of a more or less simultaneous mechanical contraction and ejection of blood from the ventricles. Delivering pacing stimulus to both ventricles is referred to as biventricular pacing while monoventricular pacing refers to left ventricular (LV) pacing, or right ventricular (RV) only pacing, often with fusion from intrinsic conduction if there is intact atrio-ventricular conduction.

CRT improves heart chamber synchrony, which is expected to enhance hemodynamic performance of the heart, such as assessed by ventricular pressure and the rate of change in ventricular pressure or other hemodynamic parameters, thereby alleviating symptoms of heart failure. Achieving a positive clinical benefit from CRT is dependent on several therapy control parameters, such as the atrio-ventricular (AV) delay and the inter-ventricular (VV) delay. The AV delay controls the timing of ventricular pacing pulses relative to an atrial depolarization, intrinsic or paced. The VV delay controls the timing of a pacing pulse in one ventricle relative to a paced or intrinsic sensed event in the other ventricle.

Selecting optimal AV and VV delays for use in controlling CRT pacing pulses may be affected by local tissue latency. Local tissue latency involves the substantially delayed response time to pace stimulation that occurs at the pace/sense lead electrode to tissue interface. Local tissue latency may be caused by diseased substrate (e.g. scar, fibrosis, etc.) or local conduction block around the site of the pacing electrode. Local tissue latency may have important implications for CRT pacing therapies. For example, if there is latency in a LV lead, it may result in simultaneous BV pacing thereby appearing as RV only pacing which is not as beneficial for the patient. A need remains, therefore, for a device and method that detects local tissue latency and, in response, adjusts one or more CRT pacing control parameters.

SUMMARY

The present disclosure is directed towards techniques for detection of local tissue latency near pacing electrodes and controlling a pacing control parameter during a pacing therapy. In particular, determination of local tissue latency is made by an implantable medical device based on timing relationships of fiducial points on an electrogram (EGM) signal in response to pacing at short atrioventricular delays. In response to determination of local tissue latency, a control parameter such as a timing parameter, e.g., an atrio-ventricular (AV) delay or an inter-ventricular (VV) delay, is controlled by an implantable medical device processor to compensate for the delay caused by latency. The fiducials on the EGM signal includes a minimum time (Tmin) associated with the minimum amplitude (Min) and a maximum time (Tmax) associated with the maximum amplitude. In one or more embodiments, a determination is made as to whether to adjust the AV delay in response to determining whether Tmin≥100 ms after delivering monoventricular pacing stimulus. In one or more other embodiments, a determination is made as to whether to adjust VV delay in response to determining whether Tmin>Tmax.

One or more other embodiments are direct to a system and method for identifying whether local tissue latency is present. The system and method comprises an implanted lead having a first electrode for cardiac pacing and sensing. A sensing module for sensing heart activity with the first electrode to produce an electrogram (EGM) waveform. A processor is configured to receive the EGM waveform and extract two or more features from the EGM waveform representative of heart activity at the electrode and identify local tissue latency at a site of the first electrode based upon at least two of the extracted features indicating local tissue latency.

The details of one or more aspects of the disclosure are set forth in the accompanying drawings and the description below. Other features, objects, and advantages will be apparent from the description and drawings, and from the claims.

DETAILED DESCRIPTION

Fundamentally, CRT alters electrical activation of the ventricles, improving spatial synchronization of electrical conduction in hearts with electrical conduction disorders such as left bundle branch block, right bundle branch block or other disorders. Optimal electrical activation of the heart may therefore be important for CRT efficacy. Optimal electrical activation can depend on a number of factors including the location of the pacing electrodes and pacing timing parameters such as AV delay and VV delay. Techniques disclosed herein enable an IMD to perform closed loop optimization of electrical activation of the heart.

Figure 1:
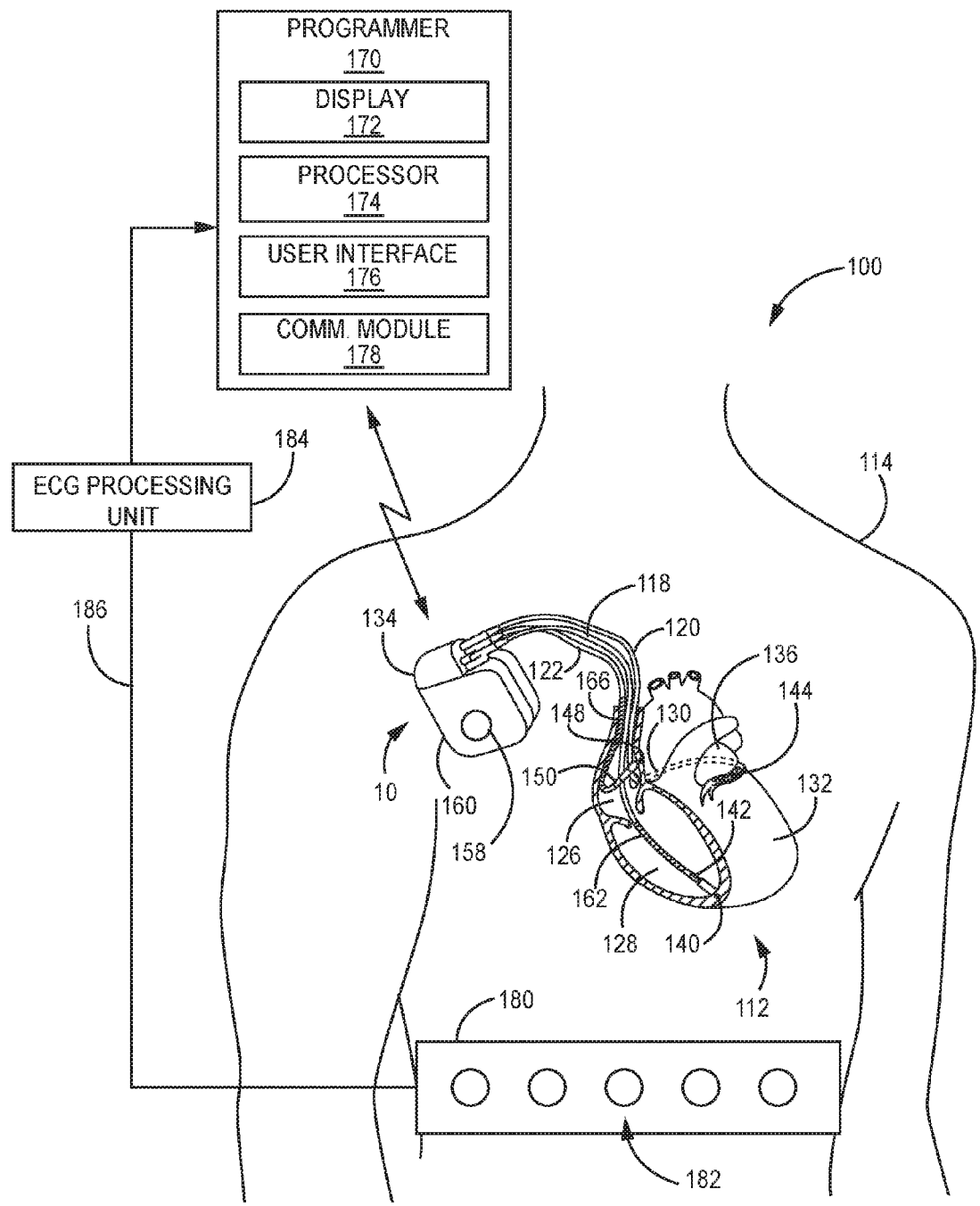
FIG. 1 is a schematic diagram of one embodiment of an implantable medical device (IMD) system in which techniques disclosed herein may be implemented.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142. CRT may be delivered by pacing in a single ventricular chamber (LV or RV) or both chambers (biventricular pacing) depending on patient need. The methods described herein are implemented in a dual or multi-chamber pacemaker or ICD delivering pacing pulses to the right and/or left ventricles using programmable pacing pulse timing parameters and selected pacing vectors.

In some embodiments, IMD 10 is configured to provide "adaptive CRT" which automatically switches between biventricular pacing and LV-only pacing in response to changes in the patient's intrinsic AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. For example, techniques disclosed herein for closed-loop optimization of a CRT control parameter may be used to optimize the AV delay applied between an atrial event, sensed or paced, and a ventricular pacing pulse delivered in one ventricle (RV or LV only) or biventricular pacing pulses (RV and LV).

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate a CRT optimization procedure performed by IMD 10 automatically or semi-automatically, to establish data for closed-loop optimization of CRT control parameters. The EGM signal is sensed using selected cardiac electrodes 140, 142, 144, 162, 166 or housing electrode 158. The EGM data are typically determined during CRT as it is delivered using varying parameter settings used to determine conduction through the cardiac tissue. By evaluating conduction through cardiac tissue response to pacing stimulus, a determination can be made as to whether local tissue latency is present. If local tissue latency was determined to be present, control parameters (e.g. AV delay, VV delay, pacing vector, pacing output etc.) can be adjusted and/or optimized by IMD 10 in a closed loop manner or through a programmer. Knowledge of a patient-specific optimal electrical condition is established using intracardiac electrodes to acquire EGM signals and/or surface electrocardiogram (ECG) electrode signals using skin electrodes in which to detect a distinctive delay between the pacing artifact (i.e. spike) and the onset of QRS. The ECG and/or the EGM is recorded for a CRT parameter setting (shortened AV delay such as 60 ms, VV delay). The EGM signal includes a minimum time (Tmin) associated with the minimum amplitude (Min) within a pre-specified time period (e.g. 160 ms, 170 ms, 180 ms, 190 ms, 200 ms etc.) In one or more embodiments, a determination is made as to whether Tmin≥100 ms during monoventricular pacing. In one or more other embodiments, a determination is made as to whether to adjust VV delay for biventricular pacing in response to determining whether Tmin>Tmax. With respect to biventricular pacing, the left ventricular pacing stimulus can be delivered ahead of right ventricular pacing stimulus by about 5 ms or more, 10 ms or more, 15 ms or more, 20 ms or more, 25 ms or more, 30 ms or more, 35 ms or more, or 40 ms or more or other suitable ranges.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS, for example as described in U.S. Pat. No. 5,683,432 (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review CRT therapy parameters and authorize programming of IMD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

While the present disclosure contemplates EGMs, acquired from intracardiac electrodes, being used to implement closed loop features of the disclosure, ECGs can also be used when implanting IMD 10 and/or during follow-up visits to the hospitals. To acquire ECGs, system 100 can further include an array of surface electrodes 182, which may be carried by a belt or strap 180 adapted to be wrapped around the torso of patient 114 to position electrodes 182 in the vicinity of heart 112. Strap 180 is shown inferior to heart 112 in FIG. 1, but it is understood that belt 180 may be positioned in a relatively more superior position to surround heart 112 such that electrodes 180 are positioned nearer to heart 112. Electrodes 182 are used to acquire surface signals from heart 112 during a CRT optimization session. A CRT control parameter (e.g. AV delay, VV delay, pacing vector, pacing output etc.) may be optimized by adjusting the parameter until the surface ECG-based determinations of ventricular activation indicate optimally synchronized ventricular activation. In one or more embodiments, EGM data is then generated by IMD 10 at the optimized parameter setting and multiple increments/decrements from the optimal delay setting to establish EGM-based local tissue latency data and its relationship to increments or decrements (e.g. 5 ms, 10 ms, 15 ms, 20 ms, 30 ms, 40 ms etc.) from optimal control parameter settings, specific to the patient. The EGM-based data is used by IMD 10 to adjust the control parameter in a closed loop to maintain optimized ventricular activation in response to detection of local tissue latency.

In one example illustrated in FIG. 1, strap 180 is wrapped around the torso of patient 114 such that the electrodes 182 surround heart 112. Electrodes 182 may be positioned around the circumference of patient 114, including the posterior, lateral, and anterior surfaces of the torso of patient 114. In other examples, electrodes 182 may be positioned on any one or more of the posterior, lateral, and anterior surfaces of the torso. Electrodes 182 may be electrically connected to an ECG processing unit 184 via a wired connection 186. Some configurations may use a wireless connection to transmit the signals sensed by electrodes 182 to ECG processing unit 184, e.g., as channels of data.

Although in the example of FIG. 1, strap 180 is shown carrying surface electrodes 182, in other examples any of a variety of mechanisms, e.g., tape or adhesives, may be employed to aid in the spacing and placement of electrodes 182. In some examples, strap 180 may include an elastic band, strip of tape, or cloth. In some examples, electrodes 182 may be placed individually on the torso of patient 114.

Electrodes 182 may surround heart 112 of patient 114 and record the electrical signals associated with the depolarization and repolarization of heart 112. Each of electrodes 182 may be used in a unipolar configuration to sense the surface potentials that reflect the cardiac signals. ECG processing unit 184 may also be coupled to a return or indifferent electrode (not shown) which may be used in combination with each of electrodes 182 for unipolar sensing. Another exemplary unipolar LV sensing/pacing vector includes LV cathode-Can (also referred to as housing). In some examples, there may be 12 to 16 electrodes 182 spatially distributed around the torso of patient 114. Other configurations may have more or fewer electrodes 182.

ECG processing unit 184 may record and analyze the surface potential signals, referred to generally herein as "ECG" signals, sensed by electrodes 182. Processing unit 184 may be configured to provide an output to a user indicating electrical conduction of heart 112. The user may make a diagnosis, prescribe CRT, position therapy devices, e.g., leads, or adjust or select treatment parameters based on the indicated electrical conduction.

ECG processing unit 184 may compute activation times directly from sensed surface potential signals. An activation time for each electrode location (of electrodes 182) may be determined as a time period between two events, such as between the QRS complex onset and the minimum derivative during the QRS signal (i.e., the steepest negative slope of the sensed potential signal) at the respective electrode. Values of one or more indices indicative of the temporal and/or spatial distribution of the activation times may be determined as measures or indicators of electrical conduction. These indicators of electrical conduction may be used to evaluate different CRT control parameters and identify an optimal CRT control parameter.

Examples of indices of cardiac electrical conduction that may be calculated from surface potential signals sensed by electrodes 182 include a standard deviation of the determined activation times, a range of activation times, and a percentage of late activations. All or a subset of the surface electrodes (e.g., only electrodes located on the left anterior, left lateral and left posterior regions of the torso) may be used for calculation or computation of the activation times. The range of activation times may be computed as the difference between the maximum and the minimum cardiac activation times determined from all or a subset of electrodes 182. The percentage of late activations estimates the percentage of electrodes 182 whose associated activation times are greater than a certain percentile, for example the 70th percentile, of the QRS complex duration or the determined activation times for electrodes 182. Techniques for determining indices of electrical conduction based on surface activation times are generally disclosed in commonly-assigned pre-grant U.S. Patent Publication No. 2012/0283587 A1 (Ghosh, et al.) hereby incorporated herein by reference in its entirety. Indices of electrical conduction derived from external surface ECG leads are generally described. CRT optimization based on such indices derived from surface ECG leads can be performed at implant or at patient follow-up visits. Techniques disclosed herein, however, enable tuning of pacing timing parameters in an ongoing closed-loop manner to maintain optimal electrical activation of the ventricles in a patient-specific manner.

One or more indices of ventricular conduction based on the surface potential signals sensed by electrodes 182 is used to identify an optimal CRT parameter setting (e.g. AV delay, VV delay, pacing vector, pacing output etc.). A user may program the control parameters into IMD 10 using programmer 170. In some embodiments, ECG processing unit 184 and programmer 170 are in wired or wireless communication or integrated in a common device that enables system 100 to automatically step through multiple CRT parameter settings, record and analyze surface potential signals to obtain one or more ECG-based indices of ventricular conduction, and identify and program an optimal setting for the CRT parameter based on analysis of ventricular electrical activations determined from surface ECG signals.

The strap 180 carrying electrodes 182 is one illustrative embodiment of an apparatus that is useful in recording surface ECG signals from which ventricular activation times can be determined. Other surface cardiac signal recording apparatus may be used for acquiring cardiac signal data from which ventricular activation times can be computed and used in computing ventricular conduction for establishing an optimal setting of one or more CRT control parameters. Other signal recording apparatus and techniques may include 12-lead ECG electrodes, a vest carrying an array of electrodes, and vectorcardiography.

Once an optimal CRT parameter is established based on optimal synchronization of electrical activation signals of the ventricles derived from surface ECG signals, CRT is delivered by IMD 10 using the optimal parameter setting and multiple non-optimal settings increased or decreased, i.e. shifted, from the optimal setting. IMD 10 acquires EGM signals for the optimal setting and multiple non-optimal settings to establish EGM parameter data for differing states of ventricular activation, i.e. different states of optimal electrical conduction of the signal through cardiac tissue (LV, RV, LA, RA) and non-optimal electrical conduction corresponding to different increments or decrements from the optimal setting of the control parameters. This EGM parameter data is stored by IMD 10 and can be used in closed-loop CRT control parameter optimization.

Figure 2:
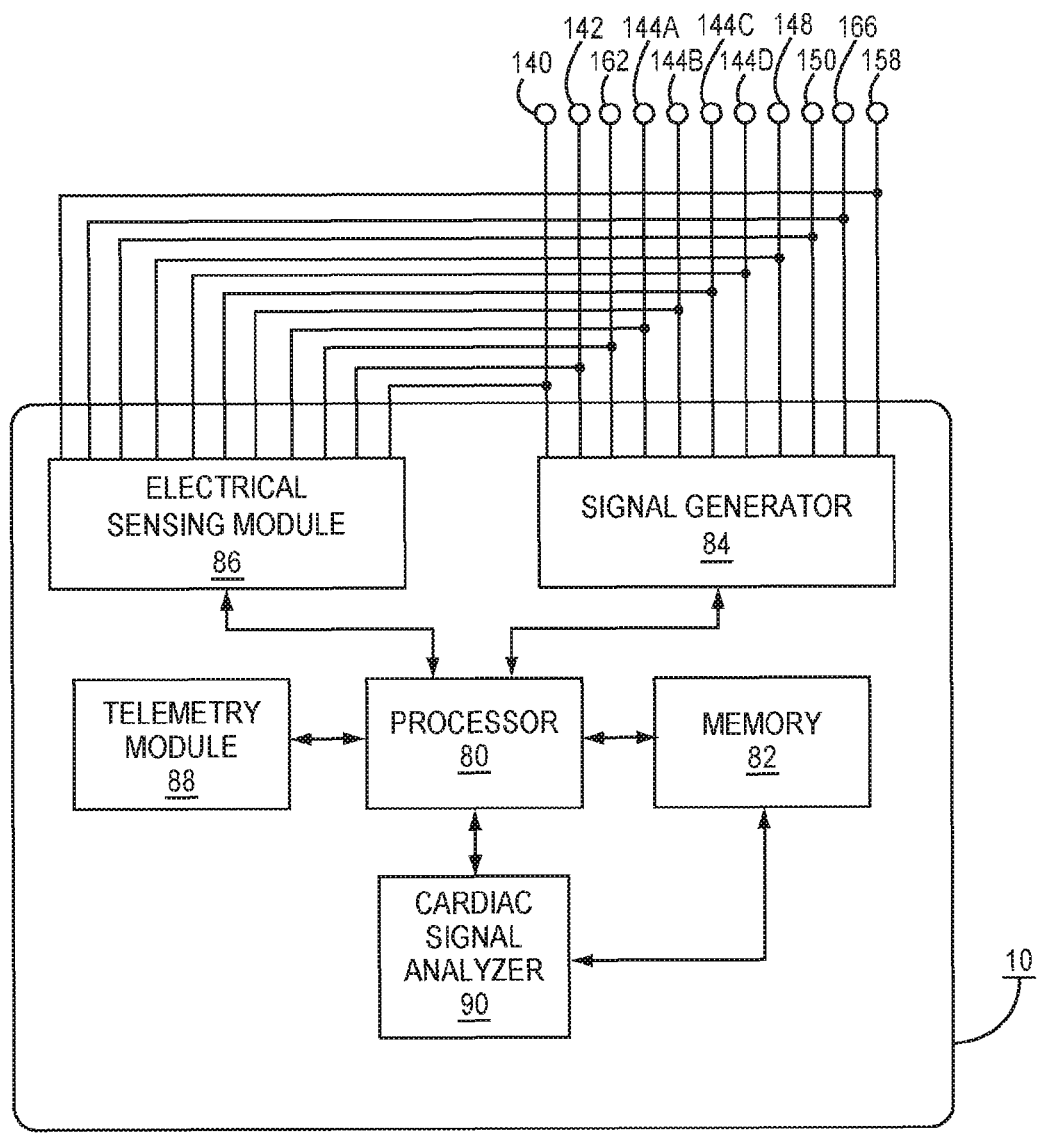
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, also referred to herein as "processor" 80, memory 82, signal generator 84, sensing module 86, and telemetry module 88. IMD 10 further includes cardiac signal analyzer 90.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory propagating signal.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to AV and/or VV delays during CRT. These delays are set based on an analysis of cardiac signals by analyzer 90 as will be described herein.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber. Sensing module 86 may further include digital signal processing circuitry for providing processor 80 or cardiac signal analyzer 90 with digitized EGM signals. An exemplary cardiac signal morphology waveform analysis method is disclosed in U.S. Pat. No. 8,738,813 published on May 27, 2014 to Ghosh et al., the disclosure of which is incorporated by reference, in its entirety. It will be appreciated that many different morphology waveform analysis methods can be used.

The occurrence of R-waves in the ventricles, e.g. in the RV, may be used in monitoring intrinsic AV conduction time. In particular, prolongation of the AV conduction time or the detection of AV block based on R-wave sensing during no ventricular pacing (or pacing at an extended AV delay that allows intrinsic conduction to take place) is used to control adaptive CRT in some embodiments. When AV conduction is impaired, signal generator 84 is controlled by processor 80 to deliver biventricular pacing, i.e. pacing pulses are delivered in the RV and the LV using a selected AV delay and a selected VV delay. When AV conduction is intact, signal generator 84 is controlled by processor 80 to deliver LV-only pacing at a selected AV delay to optimally improve conduction according to an EGM-based parameter whose relationship to ventricular electrical activation conduction has been previously established.

As described herein, the AV delay may be optimized uniquely for different heart rhythm states such as rhythm states involving atrial sensing, atrial pacing, LV-only pacing, or biventricular pacing. For example, atrioventricular rhythm states may be evaluated: 1) atrial-sensed, biventricular paced, 2) atrial-paced, biventricular paced 3) atrial-sensed, LV-only paced and 4) atrial-pace, LV-only paced. EGM-based conduction data may be established for different rhythm states and used to adjust the pacing control parameters (e.g. AV delay, VV delay, pacing vector, pacing output parameter etc.) according to the sensed EGM-based data and the current atrial sensing or pacing rhythm state and/or LV-only or biventricular pacing state.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber. Memory 82 stores look-up tables and/or equations established for adjusting CRT control parameters such as AV and VV delays as will be described herein. Equations may be stored in the form of coefficient and intercept values defining a relationship between an EGM-based ventricular conduction parameter and different settings of a control parameter.

Figure 3:
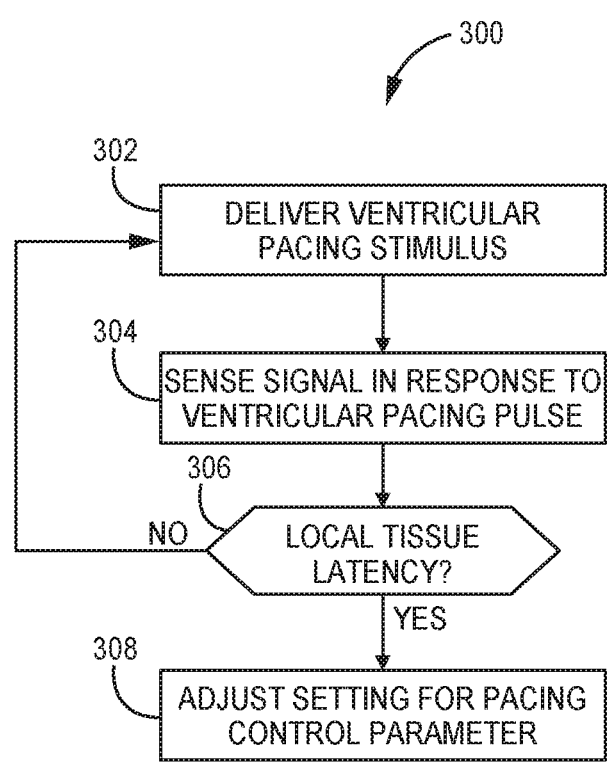
FIG. 3 is a flow chart of a method for adjusting a control parameter such as atrio-ventricular (AV) delay or inter-ventricular (VV) delay in response to determining whether local tissue latency is present.

FIG. 3 is a flow chart of a method 300 for adjusting one or more pacing control parameters in response to identifying local tissue latency exists in the area of a pacing lead. Method 300 begins at block 302 in which a ventricular pacing pulse is delivered to cardiac tissue (e.g. LV, RV) at a shortened AV delay equal to or less than 60 ms while the VV may be set to zero. The ventricular pacing pulse can be either a monoventricular pulse (i.e. LV only pacing (FIG. 4), RV only pacing) or a biventricular pulse (FIG. 5). One or more signals (i.e. EGM and/or ECG) are sensed through one or more sensing/pacing vectors in response to the delivered ventricular pacing pulse at block 304. Exemplary sensing/pacing vectors that may be used for sensing an EGM include a bipolar LV electrode (i.e. cathode) and a RV coil (i.e. anode) or a unipolar LV cathode-Can (also referred to as housing of IMD 10).

A monitoring window, immediately following a pacing pulse (or after a blanking interval), is used when acquiring data from an EGM signal. For example, the monitoring window along the X-axis can be set from 0 to about 200 ms or less, 190 ms or less, 180 ms or less, 170 ms or less, 160 ms or less, 160 ms or less etc. For the exemplary LV only pacing pulse shown in FIG. 4, the maximum amplitude is about 0.9 mv at a time of 150 ms referred to as Tmax_LV and the minimum amplitude is about 1.25 mv at a time of 100 ms referred to as Tmin_LV where both time-intervals Tmin_LV and Tmax_LV are measured from the time when the ventricular pacing stimulus was delivered. For the BV pacing pulse shown in FIG. 5, the maximum amplitude is about 4 millivolts at a time of 80 ms referred to as Tmax_BV and the minimum amplitude is about 3.8 mV at a time of 150 ms referred to as Tmin_BV.

At block 306, a determination is made as to whether local tissue latency is detected. The criterion for determining local tissue latency depends on the type of pacing (i.e. monoventricular pacing, biventricular pacing) being performed. If LV only pacing is being delivered to the left ventricle, the criterion used to detect local tissue latency is whether $Tmin \geq 100$ milliseconds. As applied to the EGM signal sensed in response to LV only pacing (depicted in FIG. 4), Tmin is equal to 100 ms and so local tissue latency is detected. If Tmin is less than 100 ms, local tissue latency is not present. If Tmin is greater than or equal to 100 ms, local tissue latency is present.

If BV pacing pulses are being delivered, the processor determines whether Tmin>Tmax. If the sensed data indicates Tmin>Tmax, local tissue latency is deemed present. Local tissue latency is not present if Tmin is not greater than Tmax. Table 1, presented below, summarizes the data acquired from EGM signals depicted in FIGS. 4-5.

TABLE 1

Figure 4:
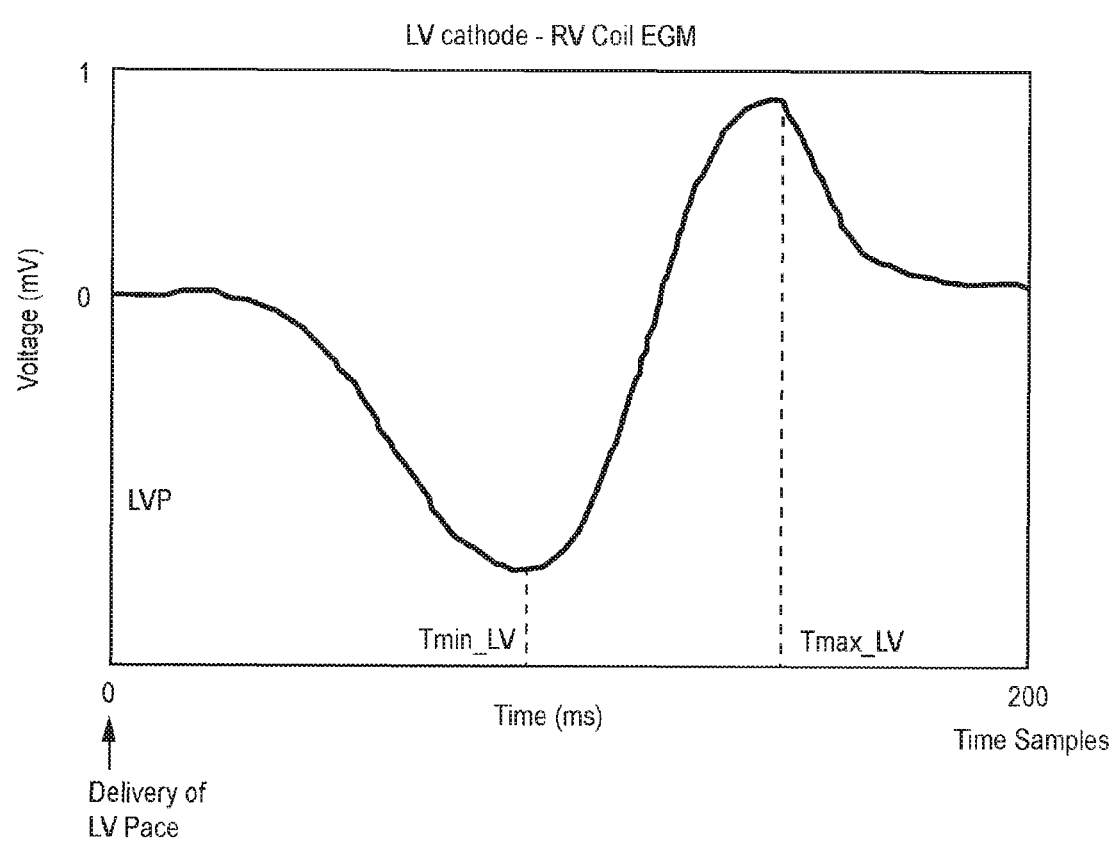
FIG. 4 is an intracardiac electrogram (EGM) signal of a paced beat acquired through left ventricular pacing only of a pacing vector.
Figure 5:
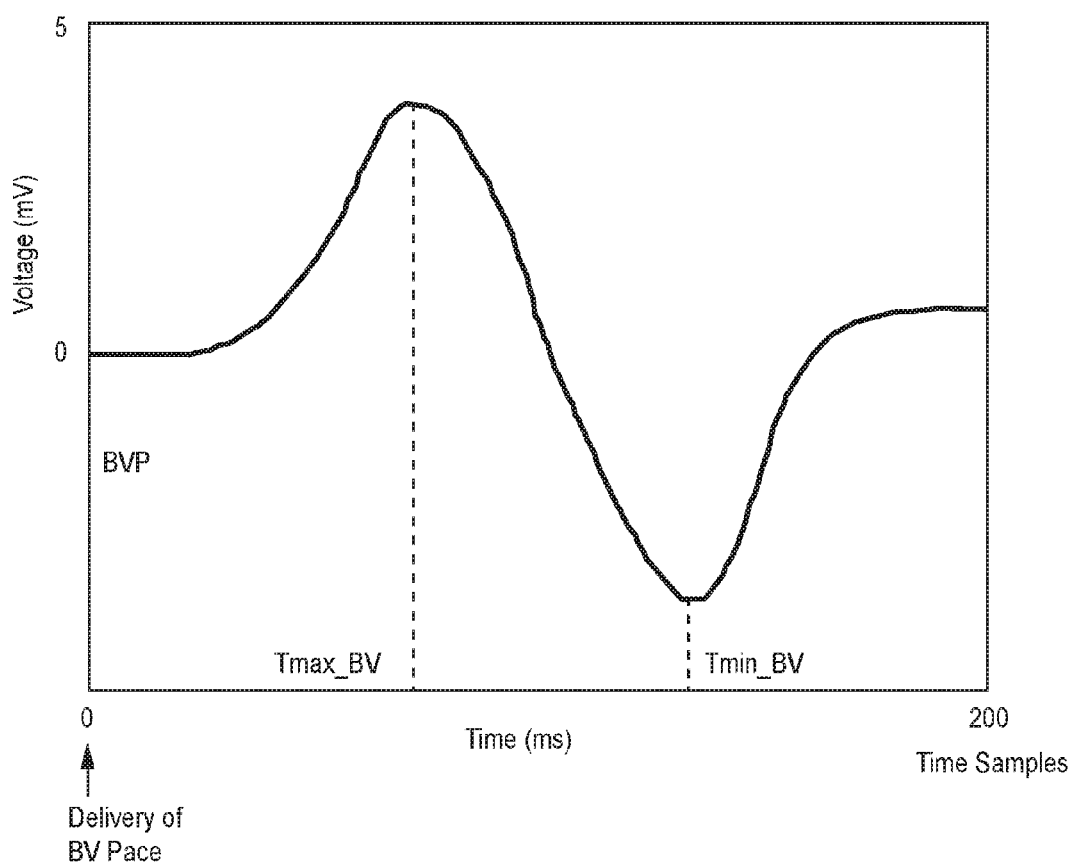
FIG. 5 is an EGM signal of a paced beat acquired through biventricular pacing of a pacing vector.

Summary of local tissue latency examples presented by the EGMs depicted in FIGS. 4-5.

| Parameter or condition | Example 3-FIG. 4 | Example 4-FIG. 5 |
| --- | --- | --- |
| Pacing | Left ventricular pacing only | Biventricular pacing |
| Tmax | 150 ms | 80 ms |
| Tmin | 100 ms | 150 ms |
| Min | 1.25 mV | 4 mV |
| Max | 0.9 mV | 3.8 mV |
| Tmin ≥ 100 ms for monoventricular pacing | Yes | Not applicable |
| Tmin > Tmax for biventricular pacing | Not applicable | Yes |

At block 308, one or more pacing control parameters is adjusted if local tissue latency is detected at block 306. For example, one of the timing parameter (e.g. AV delay, VV delay etc.) may be adjusted automatically adjusted by a decrement (e.g. 5 ms, 10 ms, 15 ms, 20 ms, 25 ms, 30 ms, 35 ms, 40 ms) or increment (e.g. 5 ms, 10 ms, 15 ms, 20 ms, 25 ms, 30 ms, 35 ms, 40 ms). Alternatively, the timing parameter may undergo an evaluation period to select an optimal timing parameter during different rhythm conditions or states, e.g. during atrial sensing and during atrial pacing (with ventricular pacing occurring in one or both ventricles). In one embodiment, AV delay is set to multiple settings during an atrial pacing rhythm and during an atrial sensing rhythm to identify an optimal AV delay during atrial sensing (SAV delay) and during atrial pacing (PAV delay).

Additionally, AV delay may be set to multiple settings during pacing in one ventricle, RV-only and/or LV-only, and during biventricular pacing. During biventricular pacing, multiple settings of VV delay may be tested. For example, once an optimal AV delay is identified using a nominal VV delay, multiple VV delay settings may be applied to determine the optimal VV delay according to an ECG data of ventricular conduction.

In some embodiments, multiple pacing vectors may be available. For example, as shown in FIG. 1, a multi-polar CS lead may include multiple electrodes available for pacing the LV. Accordingly, an optimal AV delay resulting in a minimized ventricular conduction based on surface activation time determinations may be identified for each available pacing vector. When a pacing vector is changed, for example due to a change in lead impedance or other condition, the AV or VV delay may be adjusted to an optimal setting identified for the new pacing vector.

Once an optimal setting is established for a CRT parameter, CRT is delivered at the optimal parameter setting(s). An EGM signal is acquired by sensing module 86 and provided to cardiac signal analyzer 90. Signal analyzer 90 determines a ventricular conduction parameter from the EGM signal at block 308.

An EGM-based index relative to conduction and local tissue latency can be established as a lookup table stored in memory and accessed by the processor in IMD 10. Data is stored for each test setting, along with the difference between the test (non-optimal) setting and the optimal setting for the CRT parameter at block 314. In this way, an EGM-based index is characterized for a known optimal ventricular activation condition, i.e. the optimal CRT parameter setting identified in response to surface ECG analysis, and for multiple non-optimal settings. In other words, a relationship is established between the EGM-based index and multiple parameter settings, including the optimal setting and one or more non-optimal settings different than, i.e. shifted from, the optimal setting.

Knowing the value of the EGM-based index during optimized electrical activation of the ventricles, adjustments to the CRT control parameter may be made to return the EGM-based index toward the value associated with electrical activation with excellent conduction in a closed-loop control method. The optimal control parameter setting, such as AV delay, may change with changes in heart rate, activity or other conditions. This variation in an optimal setting occurs when intrinsic AV conduction timing changes. To maintain optimal ventricular activation under changing conditions, the optimal control parameter setting, like the A-V delay, needs to be adjusted so that the relationship of the timing of a CRT ventricular pacing pulse and the timing of intrinsic ventricular conduction remains consistent. However, to determine the intrinsic AV conduction and its changes directly, ventricular pacing needs to be inhibited temporarily, suspending CRT therapy. Even short disruptions in CRT therapy may be undesirable in some patients. By monitoring the EGM-based index and its changes during CRT pacing, it is possible to detect a need to adjust a timing control parameter without temporary suspension of CRT therapy.

Adjustments to control parameters, such as timing parameters AV delay or VV delay, may be made based on the stored patient-specific relationship and local tissue latency data of the EGM-based index to increments and decrements of the control parameters. In this way, the EGM-based index can be restored to the value associated with optimal electrical activation to elicit a proper response or capture and maintained at this value regardless of heart rate, intrinsic conduction changes or other changing conditions.

To diagnose tissue latency based on the method described above, it is important to ensure that the LV or BV pacing is delivered at adequate energy that results in local tissue capture. Latency results in delayed electrical conduction due to diseased substrate near the pacing electrode which is different from inability to capture tissue because of inadequate pacing outputs. The diagnostic method advantageously employs the results from left ventricular capture management (e.g. left ventricular capture management (LVCM) etc.) to determine if the delivered energy is sufficient for local tissue capture. LVCM is a set of computer instructions, executed by the processor, that automatically monitors and, if applicable, adjusts LV output to attempt to secure ventricular capture. LVCM can minimize LV output that is delivered to capture the left ventricle, while enforcing a safety margin of amplitude over the required amplitude for ventricular capture, in order to reduce undesirable effects of electrical stimulation such as phrenic nerve stimulation. LVCM can also indicate that left ventricular capture cannot be obtained, even with high energy deliveries.

Thus, various embodiments of an IMD system and method for closed or open loop adjustment of a CRT control parameter (e.g. AV delay, VV delay etc.) have been described. However, one of ordinary skill in the art will appreciate that various modifications may be made to the described embodiments without departing from the scope of the claims. These and other examples are within the scope of the following claims.

The invention claimed is:

1. An apparatus for adjusting one or more control pacing parameters for cardiac pacing, comprising:
   (a) delivering means for delivering a left ventricular pacing stimulus at a short atrioventricular (AV) delay equal to or less than 60 ms;
   (b) sensing means for sensing a signal in response to the ventricular pacing stimulus;
   (c) processing means for determining from the signal a minimum time (Tmin) associated with a minimum amplitude;
   (d) processing means for determining whether Tmin≥100 milliseconds (ms); and
   (e) processing means for determining whether to adjust one or more control pacing parameters, in response to determining whether Tmin≥100 ms, wherein the control pacing parameters being one of AV delay, interventricular (VV) delay, pacing vector, and pacing output.

2. The apparatus of claim 1, further comprising:
   processing means for determining local tissue latency exists in response to determining that the Tmin≥100 ms.

3. The apparatus of claim 1, wherein the AV delay is shortened in response to determining that the $T_{min}$≥100 ms.

4. The apparatus of claim 2, wherein the AV delay is shortened to be less than or equal to 80 ms.

5. The apparatus of claim 2, wherein the AV delay is shortened to be less than or equal to 60 ms.

6. The apparatus of claim 2, wherein the AV delay is adjusted by a pre-specified level.

7. The apparatus of claim 6, wherein the AV delay decreased by a prespecified level being one of 5 ms, 10 ms, 15 ms, 20 ms, 25 ms, 30 ms, 35 ms, and 50 ms.

8. The apparatus of claim 1, wherein acquiring the signal comprises selecting a sensing vector comprising a left ventricular electrode and a right ventricular coil electrode.

9. The apparatus of claim 1, further comprising:
delivering means for delivering a biventricular pacing at the short AV delay.

10. The apparatus of claim 1, further comprising:
processing means for adjusting the VV delay so that the left ventricular pacing stimulus is delivered ahead of the right ventricular pacing stimulus.

11. The apparatus of claim 1, wherein the left ventricular pacing stimulus is delivered ahead of the right ventricular pacing stimulus by about 5 ins or more.

12. An apparatus for adjusting one or more control pacing parameters for cardiac resynchronization, comprising:
(a) delivering means for delivering biventricular pacing stimulus comprising a right ventricular pacing stimulus and a left ventricular pacing stimulus simultaneously at a short atrioventricular (AV) delay equal to or less than 60 ms;
(b) sensing means for sensing a signal in response to the biventricular pacing stimulus;
(c) processing means for determining from the signal a maximum amplitude (Max), a maximum time (Tmax) associated with the Max, a minimum amplitude (Min), and a minimum time (Tmin) associated with the Min, determined within pre-specified time period following the delivery of the biventricular pacing;
(d) processing means for determining whether Tmin>Tmax associated with the signal; and
(e) processing means for determining whether to adjust VV delay in response to determining Tmin>Tmax.

13. The apparatus of claim 12, comprising:
processing means for determining local tissue latency exists in response to determining that Tmin>Tmax.

14. The apparatus of claim 12, further comprising:
processing means for adjusting the VV delay so that the LV stimulus is delivered 10 ms ahead of the RV stimulus.

15. The apparatus of claim 12, further comprising:
processing means for adjusting the VV delay so that the stimulus is delivered 20 ms ahead of the RV stimulus.

16. The apparatus of claim 12, further comprising:
processing means for adjusting the VV delay so that the LV stimulus is delivered 40 ms ahead of the RV stimulus.

17. The apparatus of claim 12, wherein acquiring the signal comprises selecting a sensing vector comprising a left ventricular electrode and a right ventricular coil electrode.

18. A medical device system or determining presence of local tissue latency, the system comprising:
an implanted lead having a first electrode for cardiac pacing and sensing;
a sensing module for producing a waveform in response to delivering a pacing stimulus;
a processor configured to:
(a) setting one or more pacing control parameters including setting an atrioventricular (AV) delay to less than or equal to 60 ms,
(b) extracting two or more features from the waveform, wherein the two or more features comprise at least a minimum time (Tmin) associated with a minimum amplitude of the waveform,
(c) identifying whether local tissue latency is at a site of the first electrode based upon the at least two of the extracted features indicating local tissue latency, and
(d) in response to identifying local tissue latency, adjusting the one or more pacing control parameters.

19. An apparatus for adjusting pacing parameters for cardiac resynchronization, comprising
a) delivering a left ventricular pacing stimulus at a short AV delay equal to or less than 60 ms;
b) sensing a signal in response to the left ventricular stimulus and determining if the time-interval between the timing (Tmin) of the minimum amplitude and the time of delivery of the stimulus is 100 ms or greater, where the minimum amplitude is determined within a pre-specified time-period following the delivery of the pacing stimulus;
c) delivering a right ventricular pacing stimulus and a left ventricular pacing stimulus simultaneously at a short AV delay equal to or less than 60 ms;
d) sensing a signal in response to the biventricular pacing stimulus and determining if timing (Tmax) of max amplitude precedes timing (Tmin) of the minimum amplitude where both maximum and minimum amplitudes are determined within a pre-specified time-period following delivery of the pacing stimuli; and
e) adjusting pacing parameters in response to determining if Train for the left ventricular stimulus is 100 ms or greater than 100 ms, or if Tmax precedes Tmin for the biventricular pacing stimulus.

20. A non-transitory, computer-readable storage medium comprising instructions that, when executed, cause a processor included in a medical device system to:
(a) deliver a left ventricular pacing stimulus at a short atrioventricular (AV) delay equal to or less than 60 ms;
(b) sense a signal in response to the ventricular pacing stimulus;
(c) determine from the signal a minimum time (Tmin) associated with the minimum amplitude;
(d) determine whether Tmin≥100 milliseconds (ms); and
(e) determine whether to adjust control pacing parameters, in response to determining whether Tmin≥100 ms, wherein the control pacing parameters being one of AV delay, inter-ventricular (VV) delay, pacing vector, and pacing output.

21. A medical device system for determining presence of local tissue latency, the system comprising:
an implanted lead having a first electrode for cardiac pacing and sensing;
a sensing module for sensing heart activity with the first electrode to produce a electrogram (EGM) waveform; and
a processor configured to:
acquire or access the EGM waveform and extract two or more features from the EGM waveform representative of heart activity at the electrode, wherein the two or more features comprise at least a minimum time (Tmin) associated with a minimum amplitude of the EGM waveform, and
identify local tissue latency at a site of the first electrode based upon the at least two of the extracted features indicating local tissue latency.

22. The system of claim 21, wherein the processor is further configured to determine whether Tmin≥100 milliseconds.

23. The system of claim 21, wherein the processor further configured to adjust a pacing control parameter in response to determining Tmin≥100 milliseconds.

24. The system of claim 21, wherein the processor further configured to deliver pacing at a short atrioventricular (AV) delay equal to or less than 60 ms.

25. The system of claim 21, wherein the two or more features from the EGM waveform further comprise maximum amplitude, maximum time (Tmax) associated with the maximum amplitude, the processor further configured to determine whether Tmin>Tmax.

26. The system of claim 25, wherein the processor further configured to adjust a pacing control parameter in response to determining Tmin>Tmax, wherein the pacing control parameter being one of AV delay, inter-ventricular (VV) delay, pacing vector, and pacing output.

27. The system of claim 26, further comprising:
processing means for determining local tissue latency exists in response to determining that the Tmin≥100 ms.

28. The system of claim 26, wherein the AV delay is shortened in response to determining that the Tmin≥100 ms.

29. The system of claim 28, wherein the AV delay is shortened to be less than or equal to 80 ms.

30. The system of claim 28, wherein the AV delay is shortened to be less than or equal to 60 ms.

31. The system of claim 28, wherein the AV delay is adjusted by a pre-specified level.

32. The system of claim 31, wherein the AV delay decreased by a prespecified level being one of 5 ms, 10 ms, 15 ms, 20 ms, 25 ms, 30 ms, 35 ms, and 50 ms.

33. The system of claim 26, further comprising:
delivering means for delivering a biventricular pacing at the short AV delay.

34. The system of claim 26, further comprising:
in response to identifying local latency tissue, processing means for adjusting the VV delay so that the left ventricular pacing stimulus is delivered ahead of the right ventricular pacing stimulus.

35. The system of claim 34, wherein the left ventricular pacing stimulus is delivered ahead of the right ventricular pacing stimulus by about 5 ms or more.

\* \* \* \* \*